United States Patent [19]

Hamilton

[11] Patent Number: 5,026,027
[45] Date of Patent: Jun. 25, 1991

[54] MANUALLY ACTUATABLE SELECTOR VALVE FOR BREATH SAMPLING APPARATUS

[76] Inventor: Lyle H. Hamilton, 1034 N. 124th St., Wauwatosa, Wis. 53226

[21] Appl. No.: 591,059

[22] Filed: Oct. 1, 1990

[51] Int. Cl.$^5$ .............................................. F16K 3/04
[52] U.S. Cl. .................................. 251/301; 251/298; 251/303; 604/248
[58] Field of Search ............... 251/208, 298, 300, 301, 251/303, 313, 336; 604/248, 249

[56] References Cited

U.S. PATENT DOCUMENTS

| | | | |
|---|---|---|---|
| 1,191,700 | 7/1910 | Howes | 251/208 X |
| 1,467,615 | 9/1923 | Fairbanks | 251/313 X |
| 2,893,683 | 7/1959 | Lane | 251/313 X |
| 3,924,832 | 12/1975 | Babcock | 251/301 |
| 4,076,044 | 2/1978 | Schindling | 251/313 X |
| 4,161,307 | 7/1979 | Clinch et al. | 251/301 X |
| 4,587,989 | 5/1986 | Mayhew, Jr. | 251/208 X |

Primary Examiner—John Rivell
Attorney, Agent, or Firm—Nilles & Nilles

[57] ABSTRACT

A selector valve is disclosed for a breath sampling apparatus which comprises a pair of plate-like members that have a connection with one another for relative edgewise swinging about an axis. Each of the plate-like members has an outer surface and an inner surface which is flat and normal to the axis and which slidably opposes the inner surface of the other member. Each of the plate-like members has a port through it, the ports in the two members being spaced at like distances from said axis. A stop is provided on said members defining a first position wherein the ports are in register with one another, and a second position wherein the ports are spaced apart and wherein the port in said one plate-like member is blocked by the other plate-like member with the port in the other plate-like member open to atmosphere. A biasing spring is provided to bias the plate-like members to one of the positions. A spring bias force selector is provided to adjustably vary the force of the biasing spring.

5 Claims, 2 Drawing Sheets

MANUALLY ACTUATABLE SELECTOR VALVE FOR BREATH SAMPLING APPARATUS

FIELD OF THE INVENTION

This invention relates to improvements in selector valves for controlling flows of air and other gases that are at near-atmospheric pressures, and the invention is more particularly concerned with a manually actuatable selector valve that is especially suitable for incorporation into apparatus used for collecting breath samples that are to be analyzed for medical diagnostic purposes.

BACKGROUND OF THE INVENTION

A procedure that has come into increasing use for diagnosing certain disease conditions is collection and analysis of a sample of the exhaled breath of a patient. Breath testing is noninvasive and can be accomplished rather easily by persons who are not highly skilled. Detection of the presence of certain gases in a breath sample has been found to be a reliable indicator of conditions such as lactose intolerance, and has potential for the diagnosis of gastric or duodenal ulcer. See, for example, U.S. Pat. No. 4,947,861.

For valid diagnostic results it is necessary that the tested breath sample consist essentially only of exhaled alveolar air, that is, air that has been resident in the alveolar space and has taken part in exchange of gases with the blood stream, as distinct from air that has remained in the so-called dead air space of the oral cavity and the trachea. A conscious adult patient will usually have little difficulty in producing a satisfactory breath sample by exhaling into a mouthpiece connected with an alveolar air collection system. Alternatively, since air from the dead air space is expelled during an initial part of each exhalation, an adult patient can usually follow instructions to blow the initial part of each exhalation into the atmosphere and then breathe into a collection bag only during the last part of each exhalation, to fill only alveolar air into the bag.

However, very young children, and adults who are unconscious, or materially distracted, cannot be expected to follow such instructions, and therefore it is desirable to provide a manually controllable selector valve whereby a technician collecting a breath sample can enable the patient to breathe ambient air during inhalation, allow the first part of each exhalation to be discarded back into the air, and cause the remainder of each exhalation to be charged into a collection bag. Since a neonate or young child has a very fast respiration rate, the valve used for this purpose should be light and compact, capable of being held and manipulated with one hand to leave the technician's other hand free for other activities, and it should be operable in such a manner that the technician does not have to possess great skill nor exercise special care for successfully synchronizing the valve with the patient's respiration cycle.

The selector valve should be designed to operate in a fail-safe manner, that is, the valve should, when operated, indicate in a positive manner that it is open for transmitting a breath sample to the collection bag, and, when the valve is released for any reason, it should automatically seal the collection bag to prevent contamination of the breath sample therein.

SUMMARY OF THE INVENTION

The general object of this invention is to provide a simple, compact and inexpensive manually operable selector valve for controlling flows of air and other gases that are at near-atmospheric pressures, which valve is especially suitable for incorporation into breath sample collection apparatus because it can be conveniently held in one hand and, with the same hand, actuated to well defined alternative positions.

Another object of the invention is to provide a light, compact and inexpensive selector valve of the above described character that can be held in one hand, is biased to one of a pair of defined alternative positions, and can be quickly and accurately brought to the other of those positions by a simple squeezing motion of the hand in which the valve is held.

Another and more specific object of the invention is to provide a simple and inexpensive manually operable selector valve which achieves the last stated object and which has provision for adjusting the force that biases the valve to its said one position.

These and other objects of the invention that will appear as the description proceeds are achieved in the selector valve of this invention, which comprises a pair of plate-like members that have a connection with one another for relative edgewise swinging about an axis, each having an outer surface and having an inner surface which is flat and normal to said axis and which slidably opposes the inner surface of the other member. Each of the plate-like members has a port through it, the ports in the two members being spaced at like distances from said axis, and the port in one of the members is surrounded by a portion of the inner surface of that member which is in slidable sealing engagement with the inner surface of the other member. There are stop means on said members defining a first position of their swinging motion about said axis wherein the ports are in register with one another for communication between them, and defining a second position of their swinging motion wherein the ports are spaced apart and wherein the port in said one plate-like member is blocked by the other plate-like member and is thus sealed, while the port in the other plate-like member is open to atmosphere.

In a preferred embodiment of the invention, each of the plate-like members has a substantially round aperture through it that is concentric to the axis about which the members are relatively swingable, and these round apertures in the two members together define a spring chamber. A pilot element is mounted in the aperture of one of the plate-like members to be rotatable relative to that member; and the pilot element has a knob portion which projects outwardly beyond the outer surface of the member that carries the pilot element to be accessible for manual rotation. The pilot element has an abutment portion within said aperture on which there is a first spring anchorage that is spaced from said axis. The preferred embodiment further comprises a spring having a coiled body portion that is received in the spring chamber substantially concentrically to the axis, having one end portion secured to the first spring anchorage, and having an opposite end portion. The plate-like member other than the pilot-carrying one has means thereon defining a second spring anchorage to which said opposite end portion of the spring is secured. On the pilot element and on the pilot-carrying one of said plate-like members there are selector means cooperable to define a plurality of abutments that are alternatively and selectively engageable to releasably confine the pilot element in any one of a plurality of positions of its rotation relative to the pilot carrying member, and means for biasing said plate-like members towards one of said positions of their swinging motion under a force that is adjustably variable.

BRIEF DESCRIPTION OF THE DRAWINGS

In the accompanying drawings, which illustrate what is now regarded as a preferred embodiment of the invention.

DESCRIPTION OF THE PREFERRED EMBODIMENT

Figure 1:
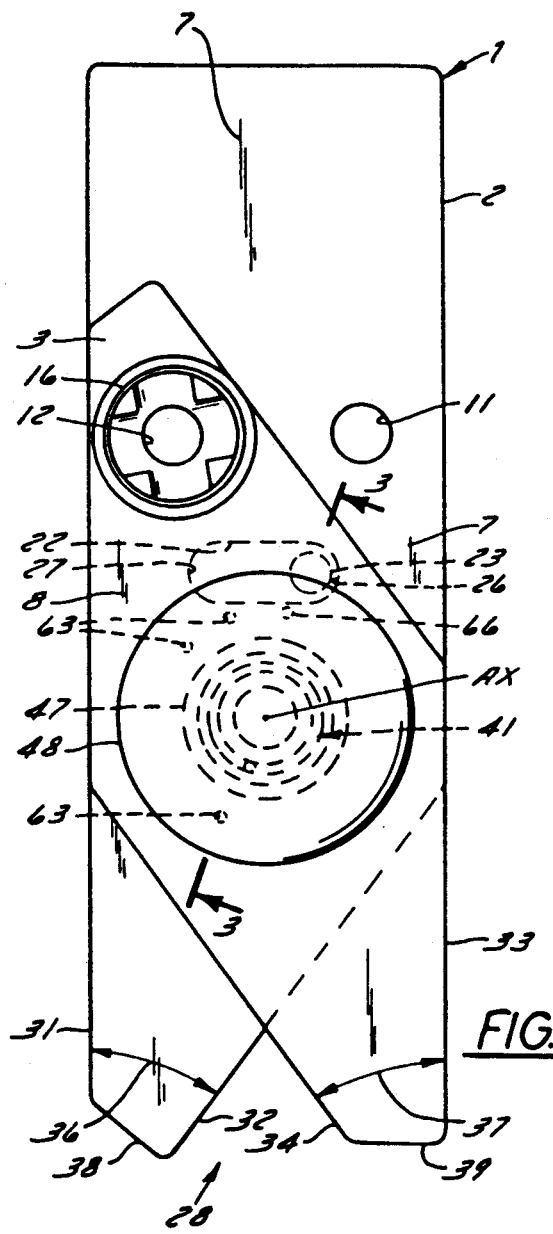
FIG. 1 is a plan view of the selector valve showing the plate-like members in one position.

Referring to the drawings, the selector valve 1 comprises first and second plate-like members 2 and 3. The plate-like members are connected by a pivot mechanism 4 (FIG. 2) for relative edgewise swinging movement about an axis AX provided by the pivot mechanism as will be more fully described hereinafter. The plate-like member 2 has an outer surface 6 and an inner surface 7. Similarly the plate-like member 3 has an outer surface 8 and an inner surface 9. The inner surfaces 7 and 9 are both flat, oriented normal to the axis AX, and in slidably opposed relation to each other.

Figure 5:
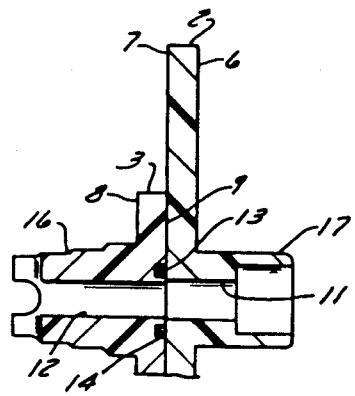
FIG. 5 is a sectional view of the selector valve taken along line 5—5 of FIG. 4.

First plate-like member 2 has a first port 11 therethrough. The second plate-like member 3 has a second port 12 therethrough. The ports 11 and 12 are spaced at like distances from the axis AX so as to be alignable with each other. The inner surface 9 of plate-like member 3 has a portion which is in surrounding relation to port 12 and which is in slidable sealing engagement with the inner surface 7 of the first plate-like member 2. As shown in FIG. 5, this sealing engagement is provided for by an O-ring 13 mounted in an O-ring receiving recess 14 in the inner surface 9 of the second plate-like member 3.

Projecting from the outer surface 6 of first plate-like member 2 is a fitting 17 that surrounds first port 11 and is adapted to be connected to a replaceable mouthpiece, not shown. A breath-sample-bag fitting 16 is mounted on plate-like member 3 in surrounding relationship to second port 12 and is adapted to be releasably connected in sealed relation to a breath sample storage bag, not shown. As known in the art, the storage bag will be made of a supple airtight material and the bag can be removed from the fitting 16 at any convenient time after the patient has exhaled into it.

Figure 4:
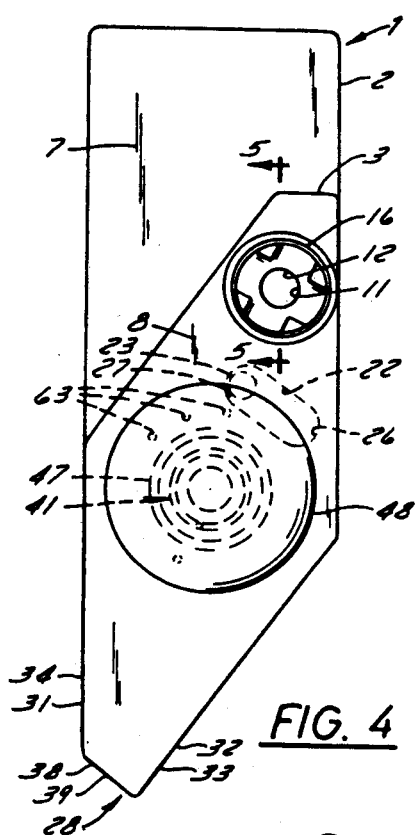
FIG. 4 is a plan view of the selector shown in FIG. 1 showing the plate-like members in another position.

The plate-like members 2 and 3 are movable about axis AX to a first position shown in FIG. 4 wherein the first and second ports 11 and 12 are in register with one another to permit communication through them, and to a second position shown in FIG. 1 wherein the first and second ports 11 and 12 are spaced apart. When the ports 11 and 12 are in the second position, the first port 11 is open to atmosphere and the second port 12 is blocked by the plate-like member 2 and is thus sealed.

The two positions of the plate-like members are determined and defined by cooperating stop means on the members. Two embodiments of the cooperating stop means are disclosed. The first embodiment of the stop means comprises a pin 23 which is mounted to project at right angles from the inner surface 7 of the first plate-like member 2. Pin 23 rides in an elongated slot 22, the ends 26, 27 of which are engaged by pin 23 to define the first and second positions.

Figure 6:
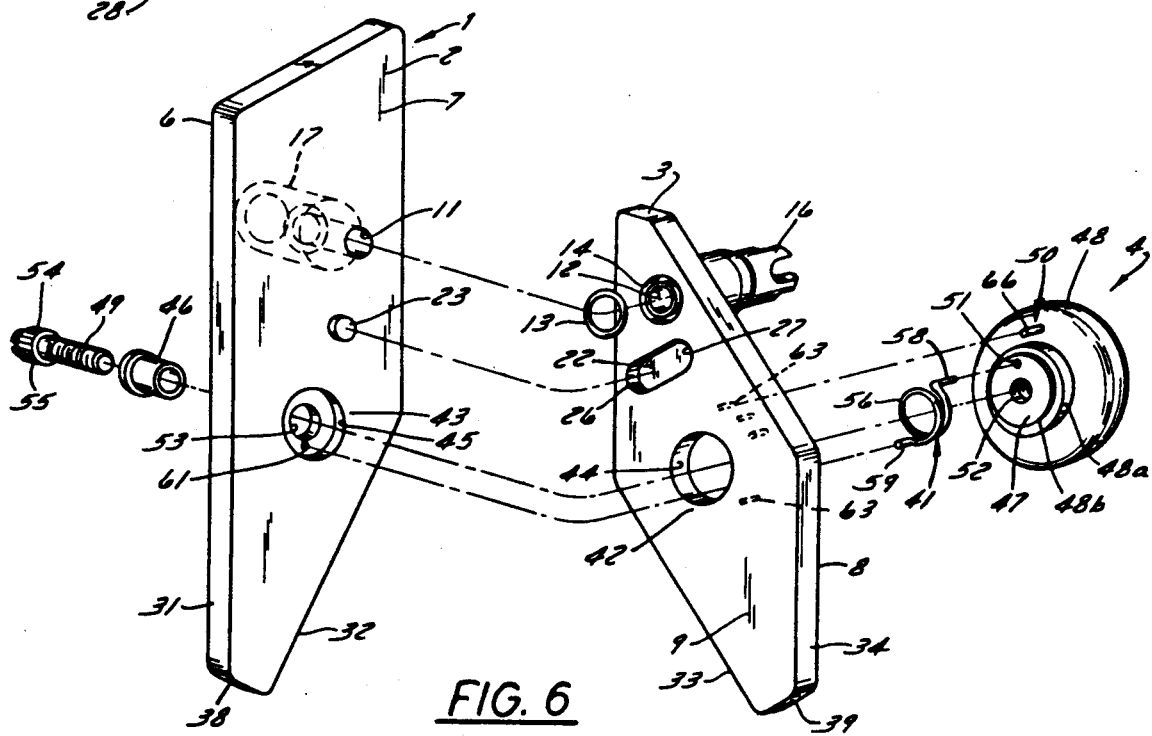
FIG. 6 is an isometric projection view of the selector valve showing the components in exploded relation to each other.

The second embodiment of the cooperating stop means comprises an alignable tactile means 28 at the actuating handle end 29 of the selector valve. With reference to FIGS. 1, 4 and 6, the first plate-like member 2 has a first outer edge 31 and a first inner edge 32. The second plate-like member 3 has a second outer edge 33 and a second inner edge 34. The included angle 36 between first outer and inner edges 31, 32 is identical to the included angle 37 between second outer and inner edges 33, 34. The first and second apex ends 38, 39 of the plate-like members 2 and 3 are at the same radial distance from axis AX when in overlying relation to each other, as shown in FIG. 4. Therefore, as the first and second plate-like members are pivoted about the axis AX, first outer edge 31 will ultimately come into exact underlying alignment with second inner edge 34, and first inner edge 32 will come into precise underlying alignment with second outer edge 33. When this alignment of outer and inner edges is achieved, the operator will feel that the plate-like members are positioned with the the first port 11 in precise register with the second port 12. Both embodiments of the stop means have been shown for purposes of illustration, but it is obvious that only one embodiment of the stop means need be employed. In addition, the outer and inner edges 31-34 are shown as straight edges and it is apparent that these edges could be contoured in any desired shape so long as they can be moved into tactilely perceptible alignment with each other when the first and second ports 11 and 12 are in register.

Figure 3:
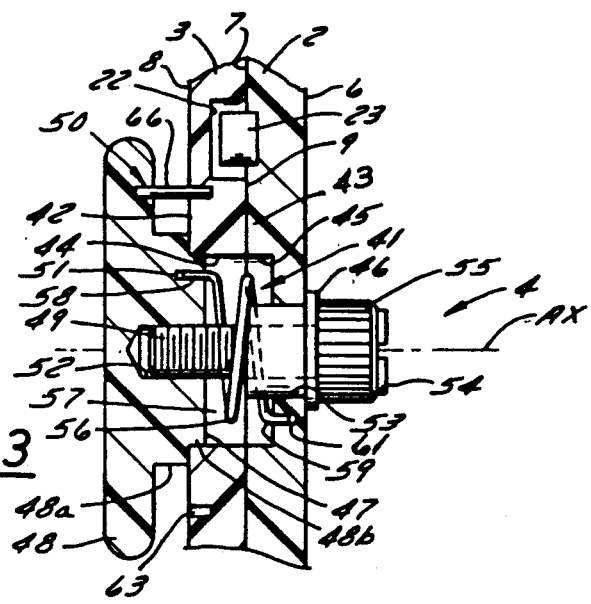
FIG. 3 is an enlarged partial view of the selector valve taken along line 3—3.

As best shown in FIGS. 1, 3 and 6, a biasing means 41 is operatively connected between the plate-like members to normally bias them towards one of their defined positions, in this case the position shown in FIG. 1 wherein first and second ports 11 and 12 are out of register. With this orientation of the biasing means 41, the valve seals off communication between the storage bag and the fitting 17 and permits such communication only when the operator deliberately moves the plate-like members 2 and 3 to the position shown in FIG. 4.

Figure 2:
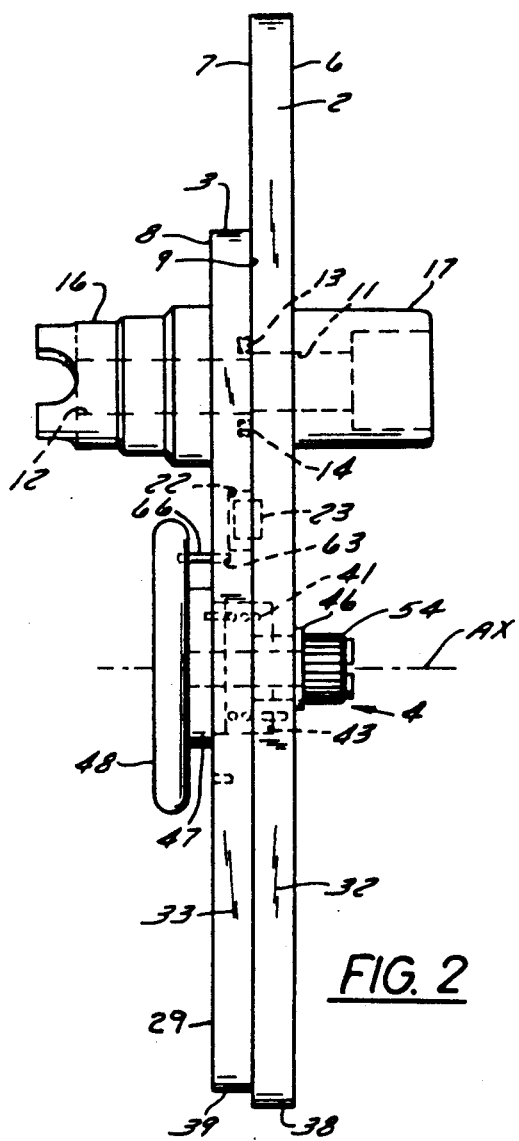
FIG. 2 is a side view of the selector valve shown in FIG. 1.

The pivot mechanism 4 that provides the connection between the plate-like members 2 and 3 comprises a pilot element 47 that has an axially outer, large diameter knob portion 48, a coaxial and axially intermediate shoulder portion 48a of smaller diameter, and a coaxial and axially innermost pilot portion 48b of still smaller diameter. As best seen in FIGS. 2, 3 and 6, the second plate-like member 3 has a central pilot-carrying portion 42 through which there is a bore 44 that is concentric to the axis AX and wherein the pilot portion 48b of the pilot element 47 is received with a close but rotatable fit. The central portion of the first plate-like member 2, which constitutes a cooperating member 43, has a counterbore 45 that opens to its inner surface and is of about the same diameter as the bore 44 and has a bore 53 which extends between its outer surface and said counterbore 45, both the bore and the counterbore being concentric to the axis AX. A bushing 46 is closely received in the bore 53 and in turn receives an adjustable retainer screw 54 which has a knurled head 55 and has a threaded shank 49 that is received in a concentric, inwardly opening threaded well 52 in the pilot element 47. If desired, a conventional shoulder bolt could be used in place of screw 54, in which case bushing 46 could be eliminated. The screw 54 constitutes a retainer means for compressively holding the first and second plate-like members together, between the pilot element 47 and the head 55 of screw 54, which is drawn against the enlarged flange of bushing 46 on outer surface 6 when the shank 49 is threaded into threaded well 52.

The biasing means 41 comprises a helical spring 56 having a coiled body portion which is received in a spring chamber 57 formed by apertures 44, 45. The coiled body portion of spring 56 surrounds the screw 54 and is substantially concentric to the axis AX. One end portion 58 of the spring is secured to a first spring anchorage 51; its opposite end portion 59 is connected to a second spring anchorage 61 on the cooperating member portion 43.

A spring bias force selector means 50 is provided on the pilot element 47 and on the pilot carrying member portion 42. The bias force selector means includes a pin 66 which projects axially inwardly from the knob portion 48 of pilot element 47, in radially outwardly spaced relation to the shoulder portion 48a, and a series of three recesses 63 which define a plurality of abutments at positions of rotation that are selectively engageable by pin 66. The pin 66 when in engagement with any one of the recesses 63 will releasably confine the pilot element 47 in any one of a plurality of positions of rotation relative to the pilot carrying member as determined by the location of recesses 63. By withdrawing pin 66 from a recess 63 axially, and rotating the pilot element 47, the force that biases the plate-like members 2 and 3 toward the position shown in FIG. 1 can be adjustably varied in accordance with the selected one of the recesses 63 into which pin 66 is inserted. In order to effect this bias force adjustment, knurled portion 55 of the screw 54 is gripped by the fingers and turned to first partially unthread the screw 54 from well 52, to allow the pilot element 47 to be moved axially away from the outer surface 8 sufficiently to permit the end of pin 66 to be removed from the recess 63. The knob 48 may then be rotated for inserting the pin element 66 into another one of the recesses 63. The screw 54 is then tightened to maintain the pin in the selected recess 63.

A compressive clamping force is exerted when screw 54 is tightened into well 52 and this compressive force is steplessly variable in order to permit the operator to control the degree of force which is required to rotate the plate-like elements 2, 3 relative to each other. In addition, the screw 54 may be fully tightened, thus locking the plate-like members 2 and 3 in their closed second position shown in FIG. 1, to prevent accidental movement of the plate-like members to an open position after the breath sample has been taken. The capability for locking the plate-like members 2, 3 in the closed second position will minimize the risk that the breath sample will be lost or contaminated by ambient air after it has been taken from the patient.

In operation, the breath sample bag is secured to fitting 16 and a mouthpiece is secured to fitting 17. The desired amount of biasing force exerted by spring portion 56 is selected by adjusting the spring bias force selector means 50, as explained above. The mouthpiece is inserted in the patient's mouth with the valve in the second position shown in FIG. 1, wherein the port 11 is open to atmosphere, thus allowing the patient to inhale and exhale normally. When the breath sample is to be taken, the initial portion of the exhalation will be allowed to vent through port 11 into the atmosphere. After initial exhalation, but while exhalation is still occurring, the operator moves the valve to the first position, shown in FIG. 4, to admit only alveolar air into the bag. When the bag contains a sufficient breath sample, or when the exhalation is complete, the operator relaxes the grip on the valve handle end 29, permitting it to again assume the second position, shown in FIG. 1, wherein port 12 is sealed. If necessary, the sampling procedure is repeated until a sufficient sample is obtained. Retainer screw 54 may be tightened to lock the valve in the FIG. 1 position, to prevent the accidental operation of the valve and consequent loss of the sample.

Disassembly of the valve may be required for sterilization purposes or for service, such as replacing the O-ring seal 13 or the spring 56. Disassembly of the valve is very easy as the plate-like members 2, 3 are held together by only the screw 54. To disassemble, knurled portion 55 of screw 54 is turned to unthread shank 49 from well 52.

From the foregoing description taken with the accompanying drawings, it will be apparent that this invention provides a simple and inexpensive selector valve for taking breath samples by relatively unskilled personnel in a manner which will minimize the risk of operator error and of losing the sample.

What is claimed is:

1. A selector valve comprising:
A. a pair of plate-like members including a pilot carrying member and a cooperating member having a connection with one another for relative edgewise swinging about an axis, each having
   an outer surface,
   an inner surface which is flat and normal to said axis and which slidably opposes the inner surface of the other of said members,
   a substantially round aperture therethrough that is concentric to said axis, said apertures together defining a spring chamber, and
   a port therethrough, said ports being spaced at like distances from said axis, the port in one of said plate-like members being surrounded by a portion of the inner surface of that member which is in slidable engagement with the inner surface of the other plate-like member;
B. a pilot element received in said aperture in said pilot carrying member for rotation relative to that member, said pilot element having
   a knob portion which projects outwardly beyond the outer surface of the pilot carrying member to be accessible for manual rotation and
   an abutment portion within said aperture having a first spring anchorage thereon spaced from said axis;
C. a spring having
   a coiled body portion received in said spring chamber substantially concentrically to said axis,
   one end portion secured to said first spring anchorage, and
   an opposite end portion;

D. means on said cooperating member defining a second spring anchorage to which said opposite end portion of the spring is secured;

E. selector means on said pilot element and on said pilot carrying member cooperable to define a plurality of abutments at positions of rotation that are alternatively and selectably engageable to releasably confine the pilot element in any one of said plurality of positions of rotation to provide a biasing of said plate-like members towards one of said positions of their swinging motion under a force that is adjustably variable; and F. cooperating stop means on said plate-like members defining a first position of their swinging motion about said axis wherein said ports are in register with one another for communication between them, and a second position of their swinging motion wherein said ports are spaced apart and wherein said port in said one plate-like member is blocked by the other plate-like member and is thus sealed.

2. The selector valve of claim 1 wherein a retainer means is releasably connected between said pilot element and said cooperating member, to normally secure said plate-like members in said slidably opposed relationship, and which is releasable to free said pilot element for axial movement away from said pilot carrying member, so that said selector means can be disengaged from an abutment it is engaged with and can be rotated about said axis for engagement with a different one of said abutments, to adjustably vary the force of said spring.

3. The selector valve of claim 2 wherein said pilot element has a threaded well and said retainer means comprises a pivot member coaxial with said axis having an engagement portion and a threaded portion threadable into said well, said plate-like members being compressively retained between said engagement portion and said pilot element with rotation of said pivot member into said well causing said threaded portion to move said engagement portion toward and away from said pilot element to vary the compressive force placed on said plate-like members.

4. A selector valve comprising:

A. a pair of first and second plate-like members having a connection with one another for relative edgewise swinging about an axis, (1) each having
an outer surface
an inner surface which is flat and normal to said axis and which slidably opposes the inner surface of the other of said members, and
a port therethrough, said ports being spaced at like distances from said axis, and (2) the port in one of said plate-like members being surrounded by a portion of the inner surface of that member which is in slidable engagement with the inner surface of the other plate-like member;

B. cooperating stop means on said members defining (1) a first position of their swinging motion about an axis wherein said ports are in register with one another for communication between them, and (2) a second position of their swinging motion wherein said ports are spaced apart and wherein said port in said one plate-like member is blocked by the other plate-like member and is thus sealed; and C. said stop means including a tactile indicating means on said plate-like members which are alignable to indicate to the user when said valve is in either said first or second positions which comprises, one of said plate-like members having first inner and outer edges spaced from said pivot axis; and the other of said plate-like members having second inner and outer edges spaced from said pivot axis the same amount as said first inner and outer edges so as to be positionable in overlying alignment with said first inner and outer edges when said valve is in at least one of said first and second positions.

5. A selector valve comprising:

A. a pair of plate-like members having a connection with one another for relative edgewise swinging about an axis, each having (1) an outer surface, (2) an inner surface which is flat and normal to said axis and which slidably opposes the inner surface of the other of said members, (3) a substantially round aperture therethrough which is concentric to said axis and which cooperates with the aperture in the other plate-like member to define a spring chamber, and (4) a port therethrough, said ports in the respective plate-like members being spaced at like distances from said axis;

B. cooperating stop means on said plate-like members defining (1) a first position of their swinging motion about said axis wherein said ports are in register with one another for communication between them, and (2) a second position of their swinging motion wherein said ports are spaced apart to be out of communication with one another;

C. a pilot element received in said aperture in one of said plate-like members for rotation relative to that member, said pilot element having (1) a knob portion which projects outwardly beyond the outer surface of said one plate-like member to be accessible for manual rotation and (2) an abutment portion within said aperture whereon there is a first spring anchorage spaced from said axis;

D. a spring having (1) a coiled body portion received in said spring chamber substantially concentrically to said axis, (2) one end portion secured to said first spring anchorage, and E. means on the other of said plate-like members defining a second spring anchorage to which said opposite end portion of the spring is secured; and F. selector means on said pilot element and on said one plate-like member cooperable to define a plurality of abutments at positions of rotation selectably engageable to releasably confine the pilot element in any one of said plurality of positions of its rotation to provide for adjustment of the force under which the plate-like members are biased towards said one position of their swinging motion.

* * * * *